United States Patent [19]

Ratajczyk et al.

[11] 3,939,161

[45] Feb. 17, 1976

[54] 1,3-DIMETHYL- 1H-PYRAZOLO(4,3-D) PYRIMIDINE-7 (6H)-ONES

[75] Inventors: James Daniel Ratajczyk, Waukegan; Robert George Stein, Kenosha; Leo Ralph Swett, Waukegan, all of Ill.

[73] Assignee: Abbott Laboratories, North Chicago, Ill.

[22] Filed: Oct. 29, 1973

[21] Appl. No.: 410,588

[52] U.S. Cl. ............... 260/256.4 F; 260/247.1 L; 260/247.2 A; 260/256.5 R; 424/250
[51] Int. Cl.$^2$........................................ C07D 239/00
[58] Field of Search............................. 260/256.4 F

[56] References Cited
UNITED STATES PATENTS

| | | | |
|---|---|---|---|
| 2,554,213 | 5/1951 | Rose | 260/256.4 F |
| 3,165,520 | 1/1965 | Schmidt et al. | 260/256.4 F |

*Primary Examiner*—Donald G. Daus
*Assistant Examiner*—J. H. Turnipseed
*Attorney, Agent, or Firm*—Robert L. Niblack; Vincent A. Mallare

[57] ABSTRACT

Novel 1,3-dimethyl-1H-pyrazolo[4,3-d]pyrimidine-7(6H)-ones. The compounds exhibit central nervous system activity, particularly anti-convulsant and sedative activity, and also exhibit anti-inflammatory activity and gastric antisecretory acitivity.

8 Claims, No Drawings

1,3-DIMETHYL-1H-PYRAZOLO(4,3-D) PYRIMIDINE-7(6H)-ONES

DETAILED DESCRIPTION OF THE INVENTION

This invention relates to novel 1,3-dimethyl-1H-pyrazolo[4,3-d]pyrimidine-7(6H)-ones which are useful as anti-convulsants, sedatives, and anti-inflammatory and gastric antisecretory agents.

The novel compounds of this invention are represented by the formula

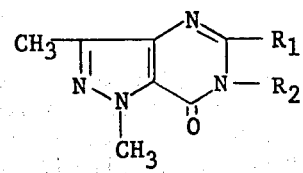

wherein $R_1$ is hydrogen, $C_1$–$C_4$ alkyl, $C_1$–$C_4$ haloalkyl, morpholinomethyl, piperidinomethyl, methoxymethyl, N-methylpiperazinomethyl, benzylthiomethyl, carbethoxy or p-chlorophenoxymethyl; and $R_2$ is hydrogen, $C_1$–$C_4$ alkyl, phenyl or substituted phenyl.

The preferred compounds of this invention are those wherein $R_1$ is methyl and $R_2$ is phenyl, substituted phenyl, or hydrogen.

The term "$C_1$–$C_4$ alkyl" includes methyl, ethyl, propyl, iso-propyl, n-butyl, sec-butyl and t-butyl.

The term "halo" includes bromo, chloro, fluoro, and iodo.

The term "substituted phenyl" as used herein, includes phenyl substituted in the ortho, meta or para position by a halo, trifluoromethyl or di($C_1$–$C_4$)alkylamino ($C_1$–$C_4$)alkyloxy atom, or a disubstituted phenyl moiety wherein the substituents are halo or methyl, for example, 2-methyl-4-chlorophenyl, 2,3-dimethylphenyl, 3,4-dichlorophenyl and the like.

"$C_1$–$C_4$ alkoxy" includes methoxy, ethoxy, propoxy and butoxy.

It will be understood that compounds wherein $R_2$ is H may exist in tautomeric equilibrium represented by the structural formulae I and II The compounds of this invention exhibit CNS activity, particularly anti-convulsant and sedative activity. The compounds are generally administered to mammalian patients in dosages of from 10 to 200 mg./kg. of body weight daily, either in single or divided doses over a 24 hour period.

In addition to the CNS activity, some of the compounds of this invention exhibit anti-inflammatory activity at dosages of from 100 to 200 mg./kg. daily, and gastric antisecretory activity at dosages of 25 to 50 mg./kg. daily. Particularly preferred anti-inflammatory agents are those wherein $R_1$ is alkyl and $R_2$ is dialkylaminoalkoxy.

The preferred gastric antisecretory agents are those wherein $R_1$ is a $C_1$–$C_4$ alkyl and $R_2$ is hydrogen. A particularly preferred gastric antisecretory agent is 1,3,5-trimethyl-1H-pyrazolo[4,3-d]pyrimidine-7(6H)-one.

In a Four-Hour Pylorus-Ligated Rat Test, the gastric anti-secretory agent of the present invention provided a significant inhibition on the acid output. For example, with dosages of between 25 and 50 mg./kg., the acid output was inhibited between about 75 and 90 percent.

The compounds of this invention are prepared by methods well known in the art. The starting material, 1,3-dimethyl-4-cyano-5-nitropyrazole, can be prepared according to U.S. Pat. No. 3,121,092 or Papesch and Dodson, J. Org. Chem. 3-, 199–203 (1965). The nitrile is hydrolyzed with an appropriate base to the carboxylic acid which is reacted with thionyl chloride to the corresponding acid chloride. The acid chloride is then reacted with an appropriate aniline or amine, followed by catalytic reduction to give the amino acid. Cyclization of the amino amides with either formic or acetic acid gives the desired product.

The preferred method of preparation is represented by the following reaction scheme:

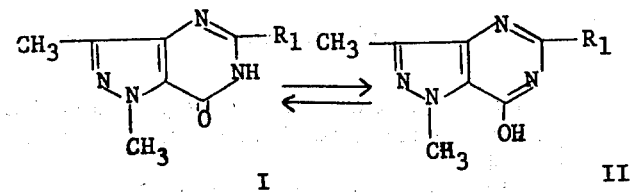

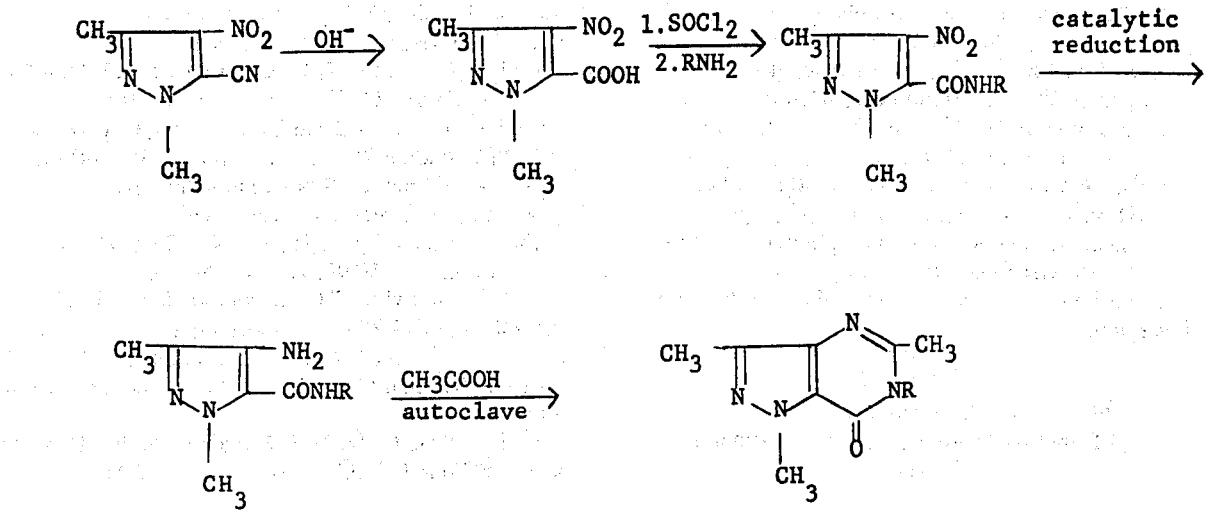

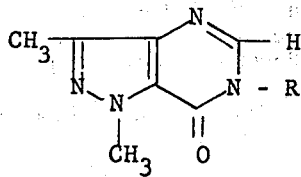

Representative compounds which can be prepared by the above reaction scheme include:

1,3-Dimethyl-5-(4-morpholinomethyl)-6-phenyl-1H-pyrazolo[4,3-d]pyrimidine-7(6H)-one.
1,3,6-Trimethyl-5-chloromethyl-1H-pyrazolo[4,3-d]-pyrimidine-7(6H)-one.
1,3-Dimethyl-5-chloromethyl-1H-pyrazolo[4,3-d]-pyrimidine-7(6H)-one.
1,3-Dimethyl-5-(1-piperidinomethyl)-6-phenyl-1H-pyrazolo[4,3-d]pyrimidine-7(6H)-one.
1,3-Dimethyl-5-methoxymethyl-6-phenyl-1H-pyrazolo-[4,3-d]pyrimidine-7(6H)-one.
1,3-Dimethyl-6-(4-bromophenyl)-1H-pyrazolo[4,3-d]-pyrimidine-7(6H)-one.
1,3-Dimethyl-5-(1-methyl-4-piperazinomethyl)-6-phenyl-1H-pyrazolo[4,3-d]pyrimidine-7(6H)-one.
1,3-Dimethyl-5-carbethoxy-1H-pyrazolo[4,3-d]pyrimidine-7(6H)-one.
1,3-Dimethyl-6-(4-chlorophenyl)-1H-pyrazolo[4,3-d]-pyrimidine-7(6H)-one.
1,3-Dimethyl-5-chloromethyl-6-(3-trifluoromethylphenyl)-1H-pyrazolo[4,3-d]pyrimidine-7(6H)-one.
1,3,5-Trimethyl-6-(4-chlorophenyl)-1H-pyrazolo[4,3-d]-pyrimidine-7(6H)-one.
1,3,5-Trimethyl-6-(2-(2-diethylaminoethoxy)-phenyl)-1H-pyrazolo[4,3-d]pyrimidine-7(6H)-one.
1,3,5-Trimethyl-6-(4-bromophenyl)-1H-pyrazolo[4,3-d]-pyrimidine-7(6H)-one.
1,3,5-Trimethyl-6-(2,3-dimethlphenyl)-1H-pyrazolo-[4,3-d]pyrimidine-7(6H)-one.
1,3-Dimethyl-5-(4-chlorophenoxymethyl)-1H-pyrazolo[4,3-d]pyrimidine-7(6H)-one.
1,3-Dimethyl-6-(2,3-dimethylphenyl)-1H-pyrazolo-[4,3-d]pyrimidine-7(6H)-one.
1,3,5-Trimethyl-6-(4-chloro-2-methylphenyl)-1H-pyrazolo[4,3-d]pyrimidine-7(6H)-one.
1,3-Dimethyl-6-(3,4-dichlorophenyl)-1H-pyrazolo-[4,3-d]pyrimidine-7(6H)-one.
1,3,5-Trimethyl-6-(3,4-dichlorophenyl)-1H-pyrazolo[4,3-d]-pyrimidine-7(6H)-one.
1,3,5-Trimethyl-6-(2-methylphenyl)-1H-pyrazolo-[4,3-d]pyrimidine-7(6H)-one.
1,3-Dimethyl-5-chloromethyl-6-(4-fluorophenyl)-1H-pyrazolo[4,3-d]pyrimidine-7(6H)-one.
1,3-Dimethyl-5-chloromethyl-6-phenyl-1H-pyrazolo-[4,3-d]pyrimidine-7(6H)-one.

The following examples further illustrate the present invention.

EXAMPLE 1

Preparation of
1,3-Dimethyl-1H-pyrazolo[4,3-d]pyrimidine-7(6H)-one 1.5 g. of 4-amino-1,3-dimethylpyrazole-5-carboxamide and 20 ml. of formic acid were refluxed for 5 hours. The reaction was concentrated in vacuo to a pink solid and triturated with ethanol to yield 1.5 g. of 1,3-dimethyl-1H-pyrazolo[4,3-d]pyrimidine-7(6H)-one, m.p. 303°–305°.

Analysis Calcd. for $C_7H_8N_4O$: C, 51.21; H, 4.90; N, 34.12 Found: C, 51.02; H, 5.37; N, 33.64.

EXAMPLE 2

Preparation of
1,3,5-Trimethyl-1H-pyrazolo[4,3-d]pyrimidine-7(6H)-one 5.6 g. of 4-amino-1,3-dimethylpyrazole-5-carboxamide and 50 ml. of glacial acetic acid were combined and heated at 185°C. for 4 hours in an autoclave. The acetic acid was removed in vacuo and water was added to the 6The crude product was filtered, washed with water and crystallized from ethanol to yield 1.6 g. of 1,3,5-trimethyl-1H-pyrazolo[4,3-d]pyrimidine-7(6H)-one; m.p. 262°–263°.

Analysis Calcd. for $C_8H_{10}N_4O$: C, 53.92; H, 5.66; N, 31.44. Found C, 54.24; H, 5.85; N, 31.49.

EXAMPLES 3–5

The following compounds were prepared according to the method of Example 2, using appropriate starting materials.

1,3,5-Trimethyl-6-(4-chlorophenyl)-1H-pyrazolo-[4,3-d]pyrimidine-7(6H)-one, m.p. 225°–227°, from 4-amino-1,3-dimethyl-5-N-(4-chlorophenyl)-pyrazolecarboxamide and acetic acid.

Analysis Calcd. for $C_{14}H_{13}ClN_4O$: C, 58.23; H, 4.54; N, 19.41. Found: C, 57.94; H, 4.79; N, 19.51.

1,3,5-Trimethyl-6-(2-methylphenyl)-1H-pyrazolo-[4,3-d]pyrimidine-7(6H)-one, m.p. 155°–158°, from 4-amino-1,3-dimethyl-5-N-(2-methylphenyl)-pyrazolecarboxamide and acetic acid.

Analysis Calcd. for $C_{15}H_{16}N_4O$: C, 67.15; H, 6.01; N, 20.88. Found: C, 66.98; H, 6.11; N, 20.99.

1,3,5-Trimethyl-6-(3-trifluoromethylphenyl)-1H-pyrazolo[4,3-d]pyrimidine-7(6H)-one, m.p. 184°–185°, from 4-amino-1,3-dimethyl-5-N-(3-trifluoromethylphenyl)pyrazole-carboxamide and acetic acid.

Analysis Calcd. for $C_{15}H_{13}F_3N_4O$: C, 55.90; H, 4.06; N, 17.38 Found C, 55.79; H, 4.20; N, 17.41.

EXAMPLE 6

Preparation of
1,3,5,6-tetramethyl-1H-pyrazolo[4,3-d]-pyrimidine-7(6H)-one 7.5 g. of 1,3,5-trimethyl-1H-pyrazolo[4,3-d]-pyrimidine-7c6H)-one were dissolved in a solution of 1.7 g. of sodium hydroxide in 50 ml. of water. The resulting solution was filtered and treated with 5.3 g. of dimethyl sulfate. The reaction mixture was allowed to stand at room temperature with occasional shaking. Within an hour, a solid separated. Water was added to the reaction, and the solid filtered, washed with water, and dried in vacuo at 85°C. to yield 5.6 g. of crude product, m.p. 194°–199°. The product was crystallized from 115 ml. of hot ethanol to yield 3.5 g. of 1,3,5,6-tetramethyl-1H-pyrazolo[4,3-d]-pyrimidine-7(6H)-one, m.p. 190°–192°.

Analysis Calcd. for $C_9H_{12}NO_4$: C, 56.24; H, 6.29; N, 29.15. Found: C, 56.44; H, 6.23; N, 29.29.

EXAMPLE 7

Preparation of
1,3-dimethyl-5-(4-chlorophenoxymethyl)-1H-pyrazolo[4,3-d]pyridmidine-7(6H)-one 15.4 g. of 4-amino-1,3-dimethylpyrazole-5-carboxamide was dissolved in 125 ml. of glacial acetic acid. 20.5 g. of p-chlorophenoxyacetyl chloride were added dropwise. The reaction mixture was brought to reflux temperature and stirred for 4 hours whereupon a crystalline precipitate formed. The reaction was allowed to stand overnight, filtered, washed with acetic acid and then with water. Recrystallization from ethanol yielded 8.2 g. of 1,3-dimethyl-5-(4-chlorophenoxymethyl)-1H-pyrazolo[4,3-d]pyrimidine-7(6H)-one; m.p. 216°–217°.

Analysis Calcd. for $C_{14}H_{13}ClN_4O_2$: C, 55.18; H, 4.30; N, 18.39. Found: C, 55.31; H, 4.22; N, 18.37.

EXAMPLE 8

Preparation of
1,3-dimethyl-6-(3,4-dichlorophenyl)-1H-pyrazolo[4,3-d]pyrimidine-7(6H)-one

A.

4-Amino-1,3-dimethyl-5-N-(3,4-dichlorophenyl)-pyrazolecarboxamide.

213 g. of the acid chloride of 4-nitro-1,3-dimethyl-pyrazole-5-carboxylic acid in 500 ml. of dry benzene was added dropwise to a mixture of 83 g. of pyridine and 170 g. of 3,4-dichloroaniline in 1 liter of benzene. The reaction mixture was allowed to stand at room temperature overnight and then filtered. The filter cake was added to 2 liters of water and the crude product collected and crystallized from 4 liters of hot ethanol to yield 232 g. of 4-nitro-1,3-dimethyl-5-N-(3,4-dichlorophenyl)pyrazole-carboxamide, m.p. 206°–208°.

Analysis Calcd. for $C_{12}H_{10}Cl_2N_4O_3$: C, 43.79; H, 3.06; N, 17.02. Found: C, 44.08; H, 3.31; N, 17.22.

The above prepared nitro amide was then catalytically hydrogenated to yield 4-amino-1,3-dimethyl-5-N-(3,4-dichlorophenyl)pyrazolecarboxamide, m.p. 223°–224°.

Analysis Calcd. for $C_{12}H_{12}Cl_2N_4O$: C, 48.18; H, 4.04; N, 18.73 Cl, 23.70. Found: C, 48.20; H, 4.36; N, 18.80 Cl, 23.53.

B.

1,3-Dimethyl-6-(3,4-dichlorophenyl)-1H-pyrazolo[4,3-d]pyrimidine-7(6H)-one 8.5 g. of the above prepared intermediate in 50 ml. of formic acid was heated under reflux overnight and cooled. A white solid was obtained. The reaction mixture was diluted with water and the solid collected and dried in vacuo at 80°. The crude product was crystallized from 200 ml. of hot methyl cellosolve and dried in vacuo to yield 7.3 g. of 1,3-dimethyl-6-(3,4-dichlorophenyl)-1H-pyrazolo[4,3-d]pyrimidine-7(6H)-one, m.p. 250°–251°.

Analysis Calcd. for $C_{13}H_{10}Cl_2N_4O$: C, 50.51; H, 3.26; N, 18.12. Found: C, 50.32; H, 3.45; N, 18.08.

EXAMPLES 9–11

The following compounds were prepared according to the method of Example 1 using the appropriate starting materials:

1,3-Dimethyl-5-carbethoxy-1H-pyrazolo[4,3-d]pyrimidine-7(6H)-one, m.p. 245°–247°, from 4-amino-1,3-dimethyl-5-pyrazolecarboxamide and diethyl oxalate.

Analysis Calcd. for $C_{10}H_{12}N_4O$: C, 50.84; H, 5.12; N, 23.72 O, 20.32. Found: C, 50.62; H, 5.02; N, 23.59 O, 20.75.

1,3-Dimethyl-6-(3-trifluoromethylphenyl)-1H-pyrazolo[4,3-d]pyrimidine-7(6H)-one, m.p. 197°–198.5°, from 4-amino-1,3-dimethyl-5-N-(3-trifluoromethylphenyl)pyrazole-carboxamide and formic acid.

Analysis Calcd. for $C_{14}H_{11}F_3N_4O$: C, 54.55; H, 3.60; N, 18.17. Found: C, 54.37; H, 3.84; N, 18.37.

1,3-Dimethyl-6-(4-chloro-2-methylphenyl)-1H-pyrazolo[4,3-d]pyrimidine-7(6H)-one, m.p. 202°–203°, from 4-amino-1,3-dimethyl-5-N-(4-chloro-2-methylphenyl)pyrazole-carboxamide and formic acid.

Analysis Calcd. for $C_{14}H_{13}ClN_4O$: C, 58.24; H, 4.54; N, 19.40. Found: C, 58.33; H, 4.83; N, 19.28.

EXAMPLES 12–29

Following the above procedures, other compounds of this invention were prepared from the appropriate starting materials. Table I below lists representative series of such compounds and their accompanying physical characteristics.

TABLE I

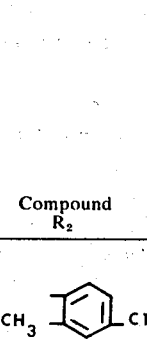

| Ex. | R₁ | Compound R₂ | Empirical Formula | Calc. % C | Calc. % H | Calc. % N | Found % C | Found % H | Found % N | M.P. in °C |
|---|---|---|---|---|---|---|---|---|---|---|
| 12 | —CH₃ | CH₃-C₆H₃-Cl | C₁₅H₁₅ClN₄O | 59.51 | 4.99 | 18.50 | 59.78 | 4.82 | 18.62 | 197–201° |
| 13 | —CH₂Cl | C₆H₄-F | C₁₄H₁₂ClFN₄O | 54.82 | 3.94 | 18.26 | 55.06 | 4.15 | 18.41 | 224–226° |
| 14 | —CH₂Cl | C₆H₅ | C₁₄H₁₃ClN₄O | 58.23 | 4.53 | 19.40 | 58.04 | 4.42 | 19.45 | 237–238° |
| 15 | -CH₂-N(morpholino) | C₆H₅ | C₁₈H₂₁N₅O₂ | 63.70 | 6.24 | 20.64 | 63.58 | 6.12 | 20.84 | 213.5–214° |
| 16 | -CH₂-N(piperidino) | —H | C₁₉H₂₃N₅O | 67.63 | 6.87 | 20.76 | 67.79 | 6.80 | 20.87 | 203° |
| 17 | —CH₂Cl | —H | C₈H₉ClN₄O | 45.18 | 4.26 | 26.34 | 45.44 | 4.29 | 26.38 | 247–249° |
| 18 | —CH₂Cl | —CH₃ | C₉H₁₁ClN₄O | 47.68 | 4.89 | 24.72 | 47.49 | 4.98 | 24.64 | 150–151° |
| 19 | -CH₂-N(N-CH₃-piperazino) | C₆H₅ | C₁₉H₂₄N₆O | 64.75 | 6.86 | 23.85 | 64.45 | 6.74 | 23.93 | 204–205° |
| 20 | -CH₂-SCH₂-C₆H₅ | C₆H₅ | C₂₁H₂₀N₄OS | 67.00 | 5.35 | 14.88 | 66.97 | 5.22 | 14.91 | 180–182° |
| 21 | —CH₃ | C₆H₃-Cl₂ | C₁₄H₁₂Cl₂N₄O | 52.03 | 3.74 | 17.34 | 52.20 | 3.55 | 17.39 | 267.5–268° |
| 22 | —CH₂Cl | C₆H₄-CF₃ | C₁₅H₁₂ClF₃N₄O | 50.42 | 3.60 | 15.67 | 50.24 | 3.92 | 15.41 | 198–205° |
| 23 | H | C₆H₄-Cl | C₁₃H₁₁ClN₄O | 56.84 | 4.04 | 20.39 | 56.81 | 3.98 | 20.58 | 222–223° |
| 24 | —CH₃ | C₆H₄-Br | C₁₄H₁₃BrN₄O | 50.46 | 3.93 | 16.82 | 51.24 | 4.43 | 16.74 | 240–242° |
| 25 | —CH₃ | C₆H₃(CH₃)₂ | C₁₆H₁₈N₄O | 68.06 | 6.43 | 19.85 | 68.01 | 6.19 | 20.05 | 208–209.5° |
| 26 | H | —CH₂CH(OCHO)—C₆H₅ | C₁₆H₁₆N₄O₃ | 61.53 | 5.16 | 17.94 | 61.74 | 5.48 | 18.04 | 144–146° |

TABLE I-continued

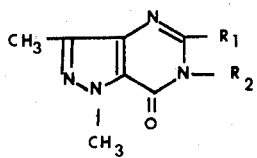

| Ex. | R₁ | Compound R₂ | Empirical Formula | Calc. % | | | Found % | | | M.P. in °C. |
|---|---|---|---|---|---|---|---|---|---|---|
| 27 | H | 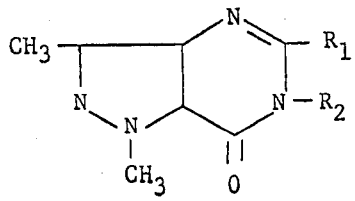 | $C_{15}H_{16}N_4O$ | 67.14 | 6.01 | 20.88 | 67.96 | 6.11 | 20.96 | 203–205° |
| 28 | —CH₂OCH₃ | 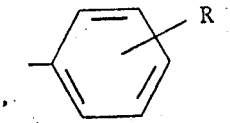 | $C_{15}H_{16}N_4O_2$ | 63.36 | 5.67 | 19.71 | 63.48 | 5.70 | 19.75 | 164–165° |
| 29 | H | 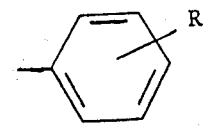 | C H BrN O | 48.92 | 3.47 | 17.55 | 49.16 | 3.53 | 17.66 | 217–220° |

EXAMPLE 30

1,3,5-Trimethyl-6-(2-(2-diethylaminoethoxy)phenyl)-1H-pyrazolo[4,3-d]pyrimidine-7(6H)-one 1,3-Dimethyl-4-nitro-5-pyrazolecarboxylic acid chloride is reacted with an equimolar quantity of o-aminophenol and the resulting nitroamide is catalytically reduced to the amino amide. Following the method of Example 2, the amino amide is cyclized with acetic acid in an autoclave and the resulting pyrazolopyrimidone is treated with an equimolar amount of diethylaminoethylchloride hydrochloride in absolute ethanol containing two equivalents of sodium ethoxide. 1,3,5-Trimethyl-6-(2-(2-diethylaminoethoxy)phenyl)-1H-pyrazolo[4,3-d]pyrimidine-7(6H)-one is obtained from the reaction mixture.

The compounds of the present invention can be incorporated into various pharmaceutically acceptable dosage forms such as tablets, capsules, pills, suspensions and the like, for immediate or sustained release, by combining them with suitable carriers or diluents according to methods well known in the art. In addition to active agent and the carrier or diluent, the dosage forms may include various excipients, binders, fillers, flavoring and sweetening agents, and the like, necessary in the formulation of the desired pharmaceutical preparation. However, in the case of filled capsules, for example, the compound can be the sole ingredient.

We claim:

1. A compound represented by the structural formula wherein R₁ is hydrogen, C₁–C₄ alkyl, C₁–C₄ haloalkyl, piperidinomethyl, methoxymethyl, N-methylpiperazinomethyl, carbethoxy, or p-chlorophenoxymethyl; and R₂ is hydrogen, C₁–C₄ alkyl, phenyl or wherein R is a substituent of the class consisting of halo, methyl, trifluoromethyl and di(C₁–C₄)alkylamino (C₁–C₄)alkyloxy.

2. A compound in accordance with claim 1 wherein R₁ is methyl and R₂ is phenyl or wherein R is a substituent of the class consisting of hal, methyl, trifluoromethyl and di(C₁–C₄)alkylamino (C₁–C₄)alkyloxy.

3. A compound in accordance with claim 1, 1,3,5-trimethyl-6-(3-trifluoromethylphenyl)-1H-pyrazolo[4,3-d]-pyrimidine-7(6H)-one.

4. A compound in accordance with claim 1, 1,3,5-trimethyl-6-(4-bromophenyl)-1H-pyrazolo[4,3-d]pyrimidine-7(6H)-one.

5. A compound in accordance with claim 1, 1,3,5-trimethyl-6-(2,3-dimethylphenyl)-1H-pyrazolo[4,3-d]pyrimidine-7(6H)-one.

6. A compound in accordance with claim 1, 1,3,5-trimethyl-6-(4-chlorophenyl)-1H-pyrazolo[4,3-d]pyrimidine-7(6H)-one.

7. A compound in accordance with claim 1, 1,3,5-trimethyl-6-(2-methyl-4-chlorophenyl)-1H-pyrazolo[4,3-d]-pyridmidine-7(6H)-one.

8. A compound in accordance with claim 1, 1,3,5-trimethyl-1H-pyrazolo[4,3-d]pyrimidine-7(6H)-one.

* * * * *